(12) United States Patent
Krahn et al.

(10) Patent No.: US 6,420,183 B1
(45) Date of Patent: Jul. 16, 2002

(54) MASKING BACKGROUND FLUORESCENCE AND LUMINESCENCE IN OPTICAL ANALYSIS OF BIOMEDICAL ASSAYS

(75) Inventors: Thoams Krahn, Hagen; Wolfgang Paffhausen, Leverkusen; Andreas Schade, Essen; Martin Bechem; Delf Schmidt, both of Wuppertal, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/194,099

(22) PCT Filed: May 23, 1997

(86) PCT No.: PCT/EP97/02662
§ 371 (c)(1),
(2), (4) Date: Nov. 20, 1998

(87) PCT Pub. No.: WO97/45739
PCT Pub. Date: Dec. 4, 1997

(30) Foreign Application Priority Data

May 28, 1996 (DE) ......................................... 196 21 312

(51) Int. Cl.$^7$ ............................................. G01N 21/00
(52) U.S. Cl. ............................ 436/164; 436/56; 436/63; 436/151; 436/166; 436/169; 436/170; 436/172; 436/517; 436/518; 436/524; 436/526; 436/528; 436/531; 436/534; 436/535; 436/800; 436/805; 436/823; 435/7.1; 435/29; 435/34; 356/317; 356/318; 356/417; 250/458.1; 250/459.1; 250/461.2
(58) Field of Search .......................... 436/56, 63, 151, 436/164, 166, 169, 170, 172, 517, 518, 524, 526, 528, 531, 534, 535, 805, 800, 823; 435/7.1, 29, 34; 356/318, 317, 417; 250/458.1, 459.1, 461.2

(56) References Cited

U.S. PATENT DOCUMENTS

| | | | |
|---|---|---|---|
| 4,476,231 A | 10/1984 | Deindoerfer et al. | 436/534 |
| 4,613,567 A | 9/1986 | Yasoshima et al. | 435/7 |
| 4,639,421 A | 1/1987 | Sage, Jr. | 435/34 |
| 4,665,024 A | 5/1987 | Mansour | 435/34 |
| 4,837,168 A | * 6/1989 | De Jaeger et al. | 436/533 |
| 4,891,324 A | * 1/1990 | Pease et al. | 436/519 |
| 5,164,301 A | 11/1992 | Thompson et al. | 435/29 |
| 5,556,764 A | * 9/1996 | Sizto et al. | 435/7.24 |
| 5,573,909 A | * 11/1996 | Singer et al. | 435/6 |
| 5,582,982 A | 12/1996 | Cubbage et al. | 435/6 |
| 5,821,066 A | * 10/1998 | Pyle et al. | 435/7.2 |
| 5,830,766 A | * 11/1998 | Attridge et al. | 436/518 |
| 5,891,733 A | * 4/1999 | Inoue | 436/63 |
| 5,928,907 A | * 7/1999 | Woudenberg et al. | 435/91.2 |
| 6,200,762 B1 | 3/2001 | Zlokarnik et al. | 435/7.1 |
| 6,214,563 B1 | 4/2001 | Negulescu et al. | 435/7.1 |
| 6,221,612 B1 | 4/2001 | Knapp et al. | 435/7.1 |
| 2001/0006820 A1 | 7/2001 | Knapp et al. | 436/172 |

FOREIGN PATENT DOCUMENTS

| | | | |
|---|---|---|---|
| DE | 3226332 | 4/1983 | G01N/33/54 |
| DE | 3213183 | 10/1983 | G01N/21/64 |
| EP | 0091046 | 10/1983 | G01N/21/64 |
| EP | 0558827 | 9/1993 | C12Q/1/04 |
| EP | 0708334 | 4/1996 | G01N/33/50 |
| GB | 2103362 | 2/1983 | G01N/33/54 |
| WO | 9302208 | 2/1993 | C12Q/1/00 |
| WO | 9323492 | 11/1993 | C09K/11/06 |
| WO | 9402642 | 2/1994 | C12Q/1/68 |
| WO | 9417388 | 8/1994 | G01N/21/01 |
| WO | WO 96/10420 | 4/1996 | |
| WO | 9745739 | 12/1997 | G01N/33/543 |
| WO | WO 98/04273 | 2/1998 | |

* cited by examiner

Primary Examiner—Christopher Chin
Assistant Examiner—Pensee T. Do
(74) Attorney, Agent, or Firm—Norris McLaughlin & Marcus

(57) ABSTRACT

In a process for the quantitative optical analysis of fluorescently labelled biological cells 5, a cell layer on a transparent support at the bottom 2 of a reaction vessel 1 is in contact with a solution 3 containing the fluorescent dye 4. The sensitivity of analytical detection can be considerably improved if to the fluorescent dye 4 already present in addition a masking dye 9, which absorbs the excitation light 6 for the fluorescent dye 4 and/or its emission light 7, is added to the solution 3 and/or if a separating layer 10 permeable to the solution and absorbing and/or reflecting the excitation light 6 or the emission light 7 is applied to the cell layer at the bottom 2. The separating layer 10 must be composed such that it has a high power of reflection for the luminescent light 11. Analogously, these process principles can also be used in receptor studies for the masking of the interfering background radiation in the quantitative optical analysis of fluorescently or luminescently labelled reaction components. In this case, a receptor layer 12 at the bottom 2 of a reaction vessel 1 is in contact with a solution in which a fluorescent or luminescent ligand 13 is dissolved. The sensitivity and accuracy of the analytical detection can be considerably improved here if a masking dye 9 which absorbs the excitation light 6 for the fluorescent dye and/or its emission light or the luminescent light is added to the supernatant 3. Instead of the masking dye in the solution 3 or optionally as an additional measure, a separating layer 10 permeable to the solution 3 and absorbing and/or reflecting the excitation light 6 and/or the emission light or the luminescent light can be applied to the cell or receptor layer 12 at the bottom 2.

28 Claims, 10 Drawing Sheets

MASKING BACKGROUND FLUORESCENCE AND LUMINESCENCE IN OPTICAL ANALYSIS OF BIOMEDICAL ASSAYS

This application is a 371 of PCT/EP97/02662, which was filed on May 23, 1997.

The invention originates from a process for the quantitative optical analysis of fluorescently labelled biological cells which are in contact with a fluorescent dye solution or of luminescent cells which are applied to a transparent support at the bottom of a reaction vessel in the form of a coherent cell layer, or alternatively of fluorescently or luminescently labelled reaction components in a solution in which a fluorescent or luminescent ligand is dissolved, the solution being in contact with a receptor layer, which is specific for this ligand and situated on the transparent support at the bottom of the reaction vessel, whose fluorescent or luminescent radiation, which is characteristic of the receptor-ligand binding, is detected and analysed through the transparent bottom.

BACKGROUND OF THE INVENTION

A problem in fluorescence measurement in biomedical assays is often that the fluorescence changes correlated with the biological cell action are small compared with the non-specific background fluorescence. As a result, the resolving power is greatly restricted. Conventional commercial measuring systems (fluorescence readers, Dynatech or SLT), cannot solve the problem, because owing to their optical measuring arrangement (excitation from 'above' through the fluorescent liquid column of the supernatant) the signal can barely be detected in comparison with the background.

Apparatuses of newer construction (Labsystems), which illuminate the cells from the back through the transparent support of the reaction vessel, do have the advantage that on entry of the excitation light the cells are excited to fluorescence. Since the excitation light, however, enters further into the supernatant, which is also fluorescent, the fact that the non-specific background signal adulterates the cell signal cannot be avoided.

Even very complicated measuring systems (NovelTech, FLIPR: Fluorescence Imaging Plate Reader) are only able to decrease this background fluorescence using a special laser illumination geometry (excitation below about 45°). The reason for the failure of all problem-solving experiments on the measuring geometry is the fact that the actual cause of the background fluorescence cannot be decisively influenced hereby.

In the receptor binding studies carried out until now using fluorescently or luminescently labelled ligands, the labelled and unbound fraction in each case must be removed by processes like washing. Many coatings, however, are sensitive to these washing steps. Moreover, the removal of the unbound ligand is associated with a considerable outlay. The direct measurement of the receptor-ligand association or dissociation is not possible in this process.

The invention is based on the object of improving the sensitivity of the optical analysis of fluorescently labelled or luminescent cells in a cellular assay in order to be able to measure, for example, membrane potential changes which are as low as possible on the basis of fluorescence changes of potential-sensitive dyes. In this case, the sensitivity of the measuring system should be so high that potential changes of below 5 mV can be detected at least qualitatively. In the case of luminescent cells, an increase in the detection of the luminescence signal should be achieved. Moreover, the method should be suitable for screening with a high sample throughput.

The invention is furthermore based on the object of simplifying receptor binding studies based on fluorescently or luminescently labelled ligands or receptors and making possible continuous measurement of the receptor binding interaction (kinetics). Owing to the reduction in the process steps necessary, this method should be particularly suitable for screening with a high throughput and for diagnostic applications.

SUMMARY OF THE INVENTION

It was only possible to achieve the required high resolution with low membrane potential changes after it was possible to eliminate the cause of the interfering overlapping of the non-specific background fluorescence and the specific fluoresence of the cells. The process according to the invention developed for this purpose is based on the fundamentally new idea of masking the excitation energy and the fluorescence not originating from the biological object. To do this, in addition to the fluorescent dye, a further dye is added which completely absorbs the excitation light of the fluorescent dye and/or its emission light without affecting the fluorescence of the cells. By means of this absorption, the non-specific background signal is masked and the useful cell signal can be detected with a resolution which was previously not possible.

An alternative solution which is within the scope of the invention is that a separating layer, which is permeable to the solution and which absorbs and/or reflects the excitation light for the fluorescent dye and/or its emission light without adversely affecting the cell properties, is applied to the cell layer. At the same time, the thickness of the separating layer is selected such that fluorescence is no longer detectable in the dissolving mixture with the fluorescent dye but without the cells.

A further variant of the invention is that the method of the separating layer according to the invention is also used for increasing the sensitivity in the quantitative optical analysis of luminescent (luminous) biological cells which are applied to a transparent support in the form of a coherent cell layer. For this purpose, the optical properties of the separating layer permeable to the solution are selected such that it reflects the luminescent light as strongly as possible without adversely affecting the cell properties. In this manner, it is possible to increase the luminescence intensity and thus the measured effect considerably.

DETAILED DESCRIPTION

The process according to the invention can be used in a completely analogous manner for the quantitative optical analysis of fluorescently or luminescently labelled reaction components in a reaction vessel filled with a solution, the fluorescent or luminescent ligand being present in dissolved form and the solution being in contact with a receptor layer which is specific for this ligand, applied to a transparent support at the bottom of the reaction vessel or deposited thereon, whose fluorescent or luminescent radiation, which is characteristic for receptor-ligand binding, is detected and analysed through the transparent bottom. In this case, the solution according to the invention of the object described above is based on the fact that the free ligand which is in the supernatant, i.e. in solution, and its non-specific fluorescence or luminescence is masked by an additional dye and/or by a diffusely absorbing or reflecting separating layer and thus the cause of the interfering overlapping of the non-specific background fluorescence and the specific fluorescence of the ligand in the solution is eliminated. Since the non-bound ligand is masked in this manner, the measured fluorescence or luminescence is a direct measure of the ligand-receptor interaction. It can be measured directly in this process with time resolution.

In receptor studies, in analogy to the process described above, the invention thus relates to a process variant in which a masking dye is added to the solution and/or a separating layer permeable to the solution is applied to the receptor layer, the optical properties of the masking dye and/or of the separating layer being selected such that the excitation light for the fluorescent dye of the ligand present in the solution and/or its emission light or its luminescent light is absorbed by the solution or the separating layer or reflected at the separating layer. In this case, the thickness of the separating layer is selected such that fluorescence is no longer detectable in the dissolving mixture with the fluorescent dye, but without the receptor layer.

The separating layer preferably consists of polymeric latex beads (e.g. polystyrene, polyurethane, butadiene, acrylonitrile). The latex beads can also be dyed with a masking dye, which in this case must have an adequately high polymer dyeing capacity.

In the first-mentioned process, the masking dye should be as well distributed as possible in the solution which also contains the fluorescent dye in dissolved form. Since, as a rule, the solvent is water, a masking dye is expediently employed which possesses good water solubility (>2 g/ml) and has no cytotoxic side effects.

According to a further development of the invention, after the replacement of the supernatant containing a fluorescent dye by a fluorescent dye-free solution, a further masking dye is added which suppresses a non-specific fluorescence on the reaction vessel wall.

The following advantages are achieved using the invention: The new process described is not tied to a certain measuring system, but can be used, because it is not a specifically technical solution, by many commercially available apparatuses. These include virtually all fluorescence readers which can illuminate and also measure transparent reaction vessels, e.g. microtitre plates, from the bottom. With a very low outlay (minimal additional costs only for the special absorption dyes), it is possible for the first time by this means to advance in a resolving area, e.g. in the measurement of potential changes in cell membranes by measurement of the change in fluorescence of potential-sensitive fluorescent dyes, which was unachieved until now. For the first time it is possible even in the case of very low changes to carry out a direct comparison of the results from various reaction vessels (e.g. various wells in a microtitre plate), such that the complicated procedure of the determination of the relative change in a reaction vessel can be dispensed with. As a result the number of measurements to be determined, e.g. for kinetic measurements, decreases. The outlay in terms of time for a measuring programme is markedly reduced and the possibility created of obtaining identical results by a simple individual measurement (e.g. end point determination) with the use of reference to a separate control batch. The uniformity of the biological batch required in this case (e.g. homogeneous cell layer) is generally afforded, for example, for microtitre plates.

Surprisingly, the use of various water-soluble dyes and also their mixtures in the very different cells tested showed no negative effect on the physiology of the cells (e.g. reaction of the cells in comparison with electrophysiological measurements such as whole-cell patch-clamp, or effects of the pharmaceuticals investigated). The use of undissolved dye pigments or inorganic finely divided particles was also surprisingly well tolerated by the biological objects.

As a result of the simple process described for masking the background fluorescence in quantitative fluorescence measurement in biomedical assays, connected with an increase in the sensitivity, e.g. when using potential-sensitive fluorescent dyes, and the adaptability of this process, e.g. to microtitre plates as reaction vessels, the use of such measuring techniques will significantly simplify high-throughput screening, especially as no increased technical expenditure is necessary for the realization of the advantages outlined, but existing commercial measuring apparatuses are sufficient for this purpose. In receptor-ligand studies, the advantage essential to the invention is that, on account of the masking of the non-specific fluorescence or luminescence, it is no longer necessary to remove the unbound fraction of the ligands. As a result, the test procedures are considerably simplified, damage to and destruction of the sensitive coatings or of the biological objects such as, for example, cells are avoided and the sensitivity and thus also the accuracy of the measurement are improved. As a result of the use of microparticles, the utilizable surface area for the coating of fluorescently or luminescently labelled ligands can be significantly increased. By means of suitable measures, e.g. relatively high specific density or the use of magnetizable particles, the settlement and concentration of the microparticles on the transparent support can be achieved. In this case too, the fluorescence or luminescence of the unbound ligands in the supernatant is effectively suppressed by the masking.

Since the interaction between the ligands and the receptor must not be interrupted by the removal of the unbound fraction, a continuous measurement of the interaction between ligand and receptor (kinetics) can be carried out in this manner even in an individual reaction batch.

BRIEF DESCRIPTION OF THE DRAWINGS

The invention is explained in greater detail below with the aid of working examples and drawings, wherein FIG. 1 shows a reaction vessel 1 for a fluorescence assay with a transparent bottom 2. A fluorescent dye solution 3, in which the fluorescent dye molecules 4 are indicated schematically, is found in the reaction vessel 1. The solution 3 is also designated as the supernatant. The biological cells to be investigated are arranged on a transparent support on the transparent bottom 2. Light (excitation light) 6 is shone through the bottom 2 in order to excite the cells 5 to fluorescence. A background fluorescence radiation 8, which originates from the likewise excited fluorescent dye molecules 4 in the supernatant 3, overlaps the fluorescent light 7 emitted by the cells 5. Only the fluorescent light 7, however, is decisive for the bioanalytical investigation and analysis of the cells 5. Since, however, in all known fluorescence analysis apparatuses the background fluorescence 8 is additionally determined, small fluorescence differences of the cells 5 are lost in the strong background fluorescence 8, which leads to a marked sensitivity loss.

Figure 1:
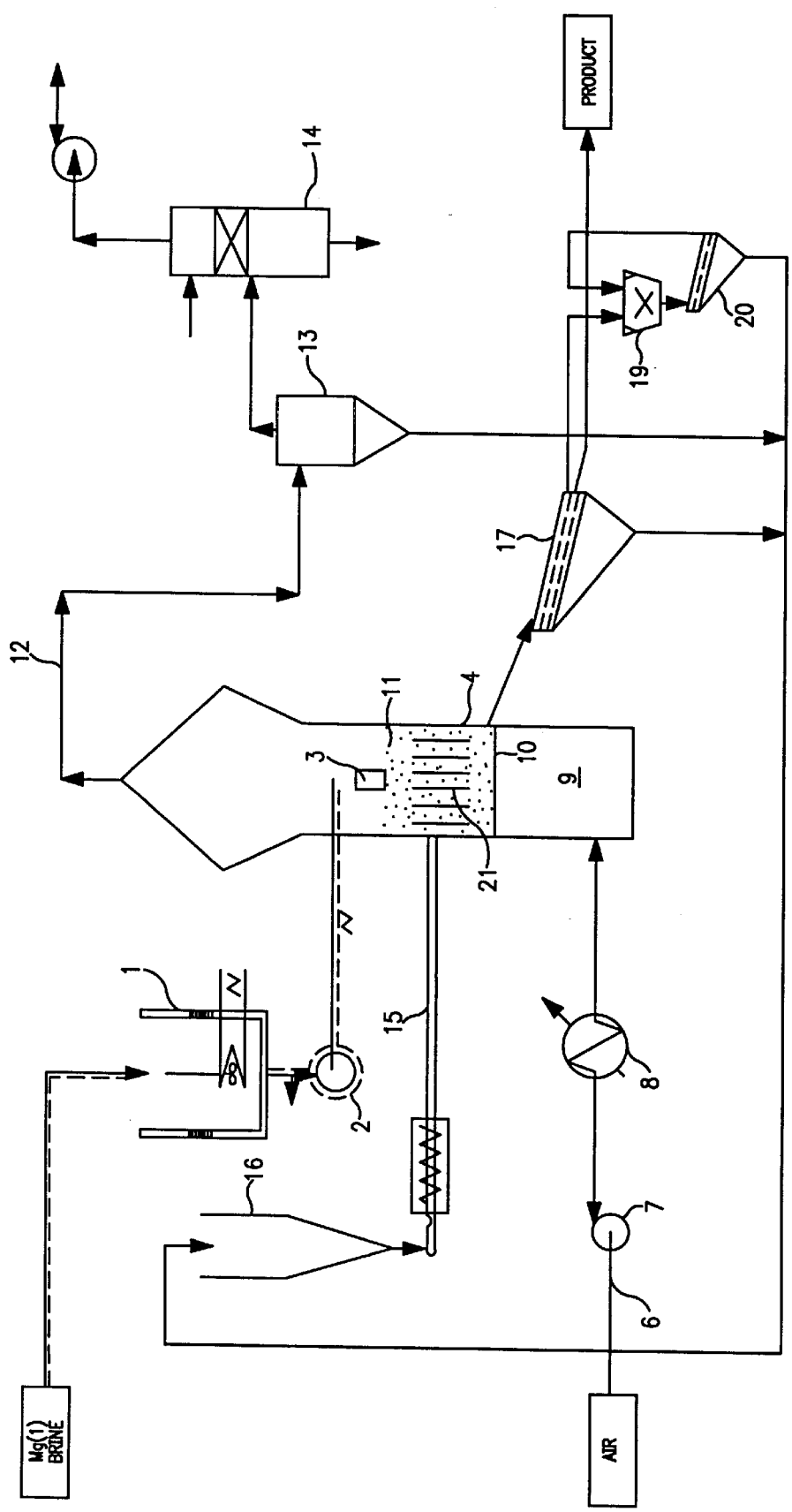
FIG. 1 shows a reaction vessel for a fluorescence assay according to the prior art
Figure 2:
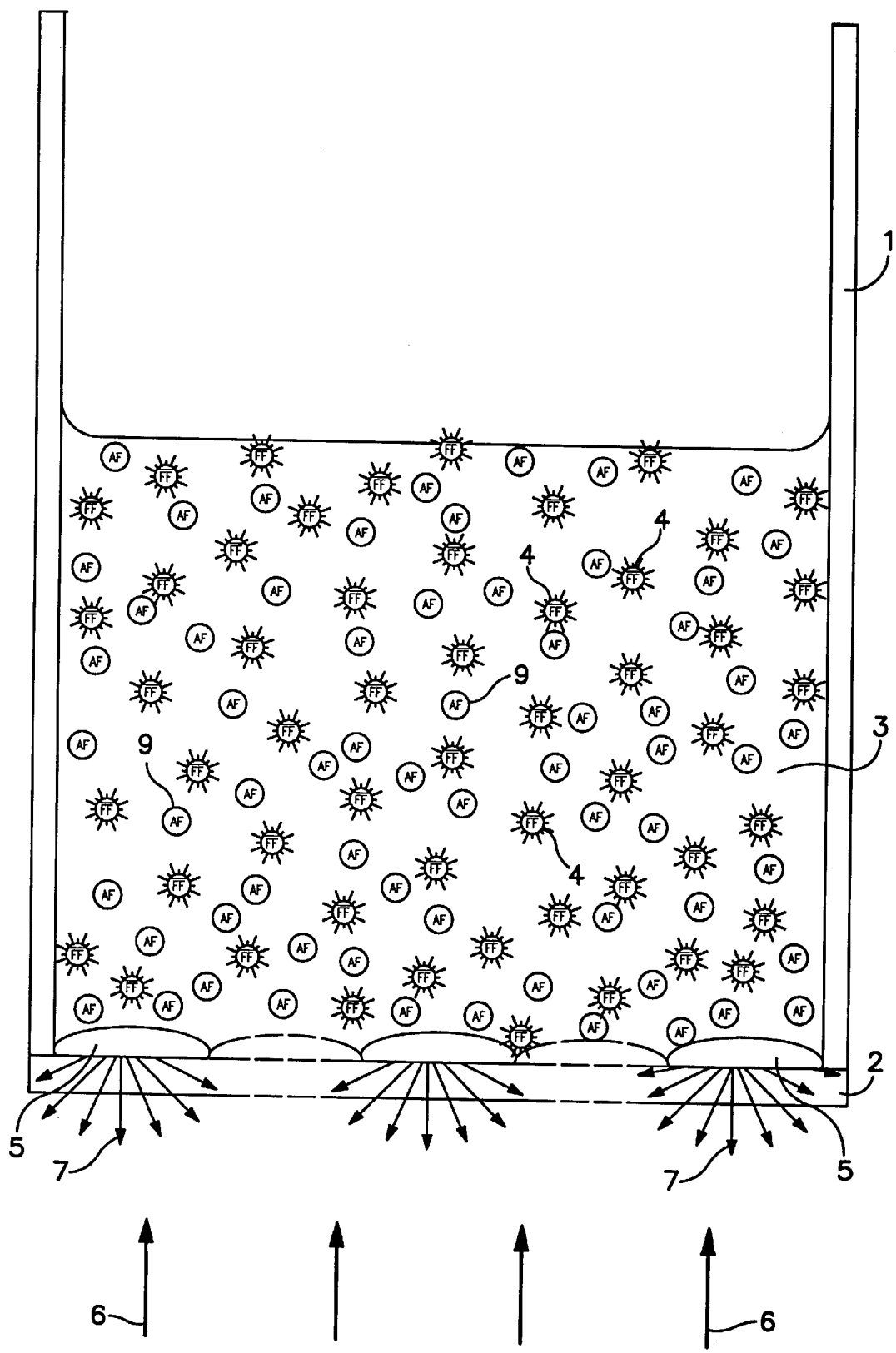
FIG. 2 shows the suppression of the background fluorescence in a fluorescence assay with a masking dye in the supernatant

This disadvantage can be avoided by the procedure according to the invention of FIG. 2 by suppressing the background fluorescence by a masking dye in the supernatant 3. The background fluorescence 8 present in FIG. 1 is completely absorbed in the supernatant according to FIG. 2. The masking dye (schematically designated by 9) added to the supernatant 3 can either be present in dissolved form or in finely divided disperse phase (colour-pigmented systems). Preferably, however, soluble dyes are employed, because in this case the addition can be carried out particularly simply with the aid of a pipette and because, in contrast to a pigment system, the physical effects of particle size distribution and of sedimentation processes and layer thickness inhomogeneities do not have to be taken into account.

The following demands are made on the properties of a dye of this type:
when using a soluble absorption dye, good water solubility for use in biological assays
no membrane permeability of the dye in order to avoid staining of the cells high specific absorption in the excitation and/or emission wavelength range of the fluorescent dye
no toxic side effects (avoidance of cell damage)

Figure 3:
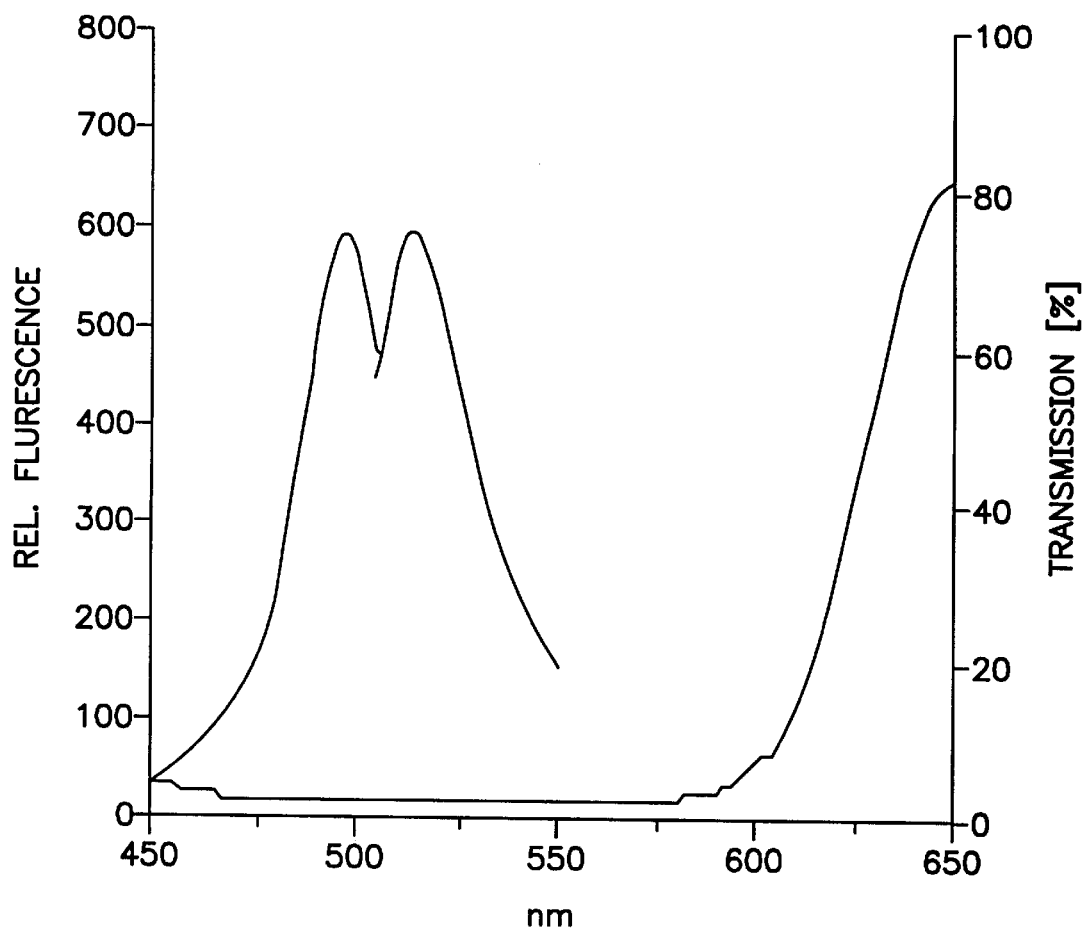
FIG. 3 shows the spectral excitation and emission for a dispersion dye and the spectral absorption of the masking dye

A solubility of >2 mg/ml is regarded as good water solubility. The cell toxicity can be determined with the aid of known test procedures (e.g. cytotoxicity test). FIG. 3 shows the optical (spectral) properties of a fluorescent dye and of a masking dye in a graph. Curve A shows the spectral distribution of the excitation light, curve B the spectral distribution of the emitted fluorescent light for the commercially available dispersion fluorescent dye bis(1,3-dibutylbarbituric acid)trimethaneoxonol ($Dibac_4(3)$) and curve C the spectral transmission (absorption spectrum) of the masking dye used (Brilliant Black BN, C.I. 28440, Food Black 1, e.g. Sigma B-8384). It is recognized that the masking dye is almost completely absorbed in the wavelength range of the excitation and emission of the fluorescent dye.

Figure 4:
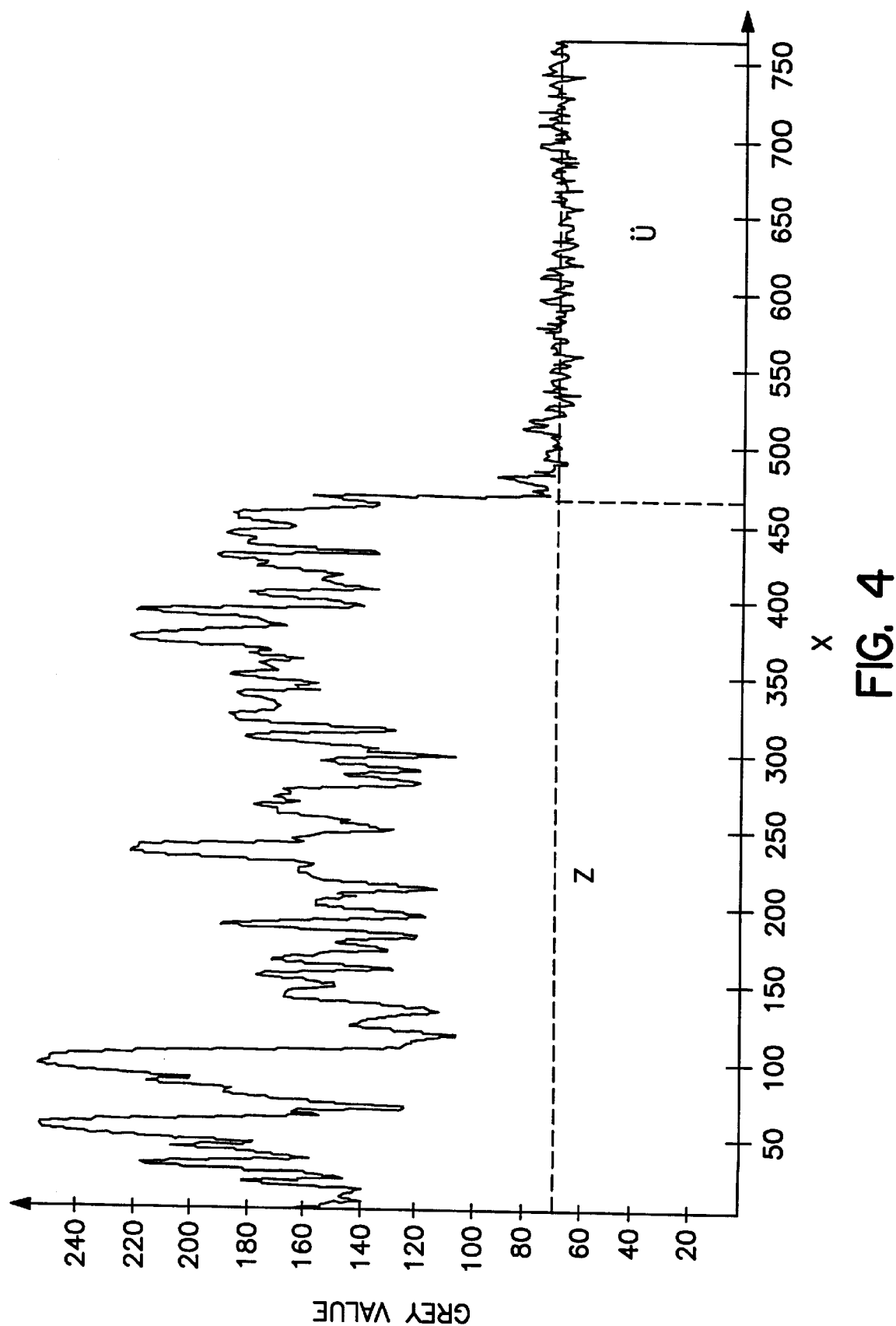
FIG. 4 shows the site-dependent cell fluorescence without masking dye
Figure 5:
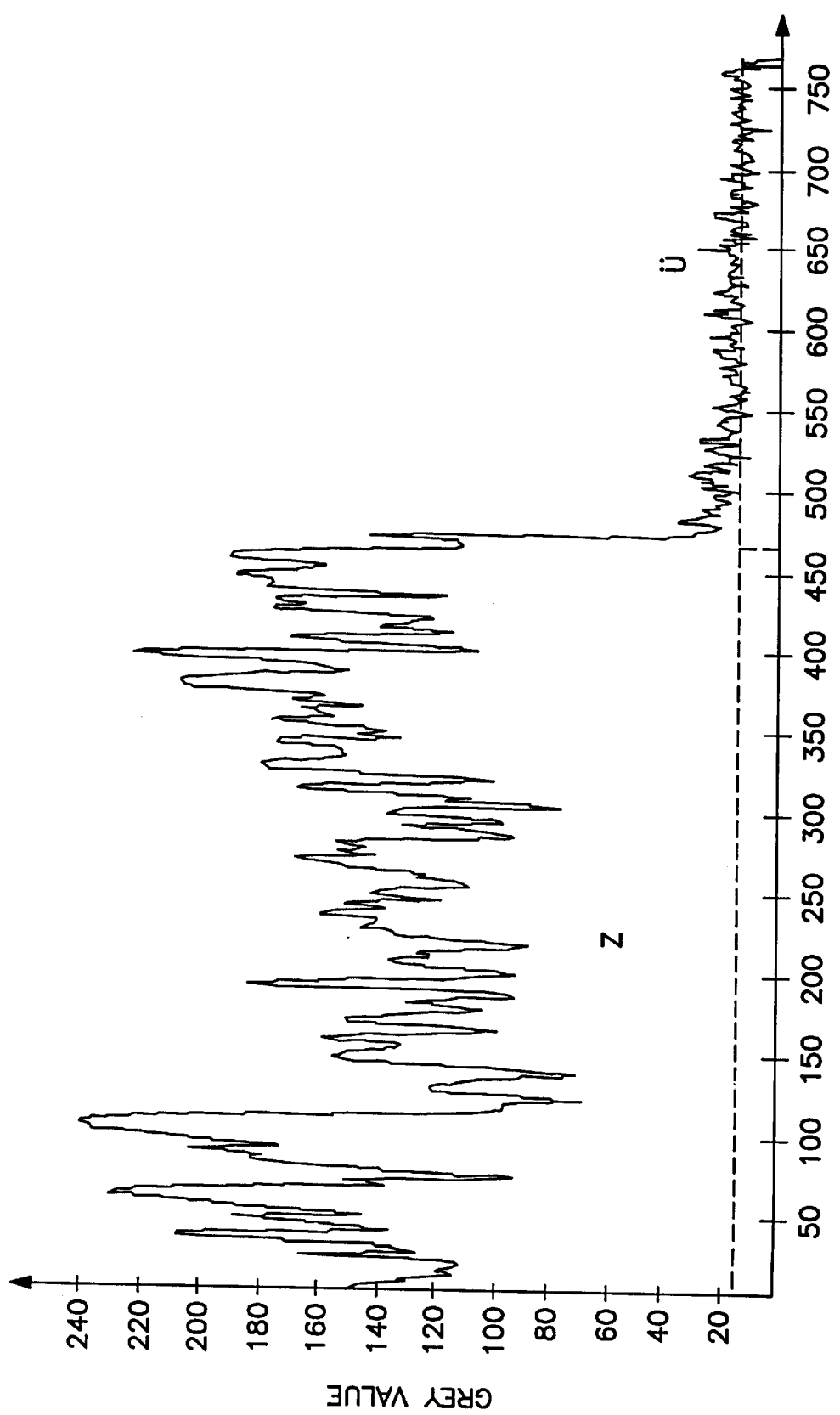
FIG. 5 shows the site-dependent cell fluorescence with masking dye

Contrast enhancement or increase in sensitivity can be even better understood with the aid of FIGS. 4 and 5. To demonstrate the action of the masking dye on the non-specific background fluorescence, two video recordings of the same image section were made before and after adding 100 mg/ml of the soluble masking dye Brilliant Black in the presence of the potential-sensitive fluorescent dye $Dibac_4(3)$ (5 mM). Both times, the same video line was assessed by image analysis and the two fluorescence intensity profiles shown over the identical sections in the reaction vessel. The region Z in this case corresponds to the region in which the cell layer, i.e. the biological sample, is found, while right of this in the zone Ü, to the greatest part, the fluorescence signal originating from the supernatant is measured. The measuring range of the recording system (8 bit) is between 0 (black) and 255 (white). For the unmasked recording, a contrast ratio of about 1:3.6 results (intensity ratio of the darkest and lightest image portions) and in the case of the masked recording a contrast ratio of about 1:14.4. This corresponds to a contrast increase by a factor of 4.

Figure 6:
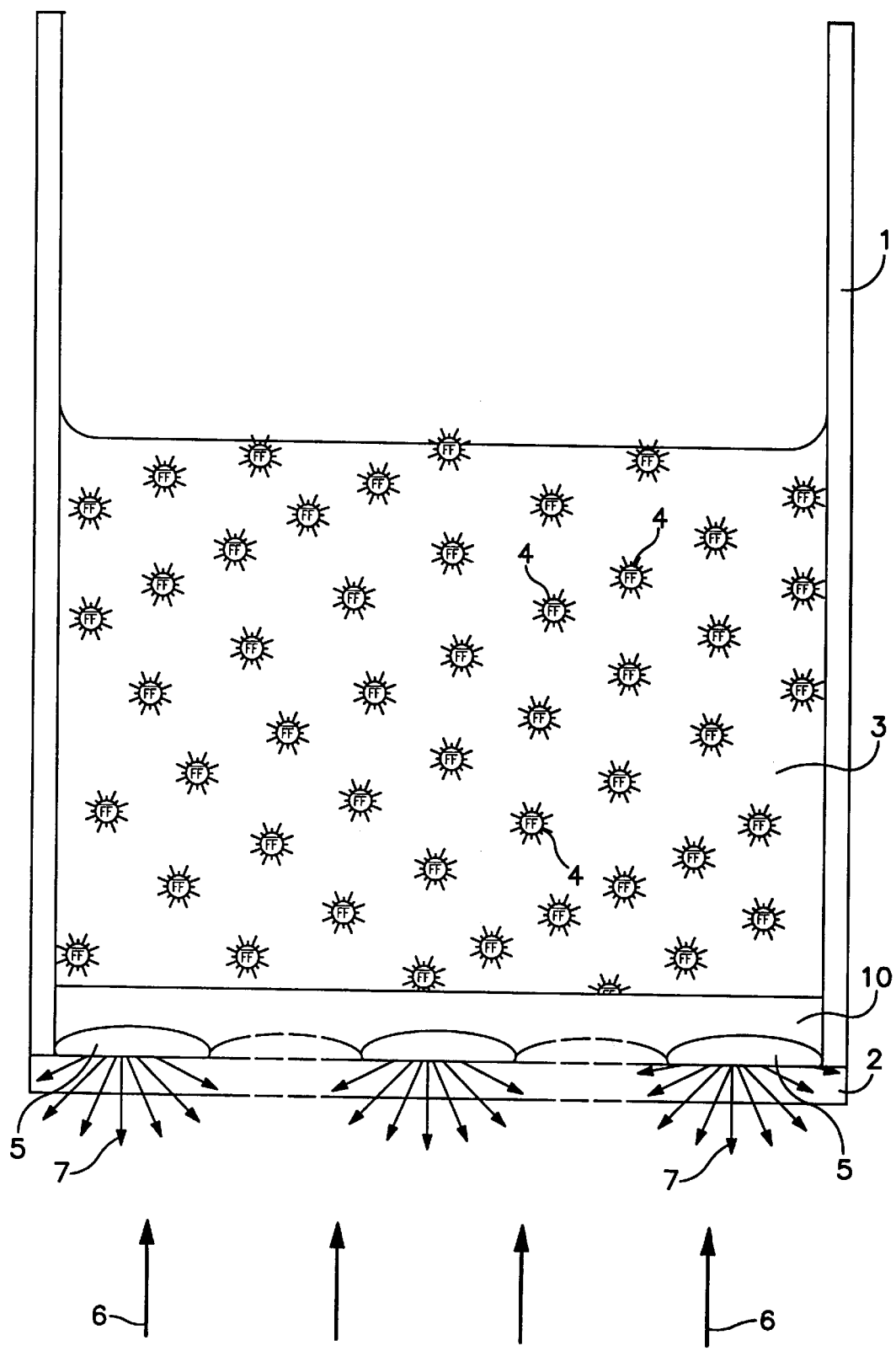
FIG. 6 shows the suppresion of the background fluorescence in a fluorescence assay with the aid of a separating layer

According to FIG. 6, an alternative possibility of improving the ratio of useful to background signal is covering of the cell layer with a finely divided optical separating layer 10. The separating layer 10 expediently consists of a finely divided inorganic white pigment, such as, for example $TiO_2$ or $Al_2O_3$. By means of this, not only the background fluorescence radiation from the supernatant 3 is screened off, but also the measurable quantity of cell fluorescence is increased by reflection from the inorganic particles.

Alternatively, the separating layer can consist of polymeric latex beads having a diameter preferably in the range from 200 nm to 5 mm. Suitable polymers are, for example, polystyrene, polyurethane, butadiene, acrylonitrile. The latex beads can also be dyed with a suitable masking dye to which the same criteria apply as for the absorption dye added to the solution (see above). A suitable class of dye is, for example, ®Resoline.

In luminescence assays (luminous cells), the requirements fundamentally consist of detecting the specific very low light intensity of a biological cell with high sensitivity. By applying a reflecting separating layer 10 according to FIG. 7, it is possible, analogously to the method for suppression of the background fluorescence (according to FIG. 6), to increase the luminescence signal of the biological cells. In this connection, radiated fractions 11 of the undirected luminescent light are reflected in the direction of the detector and thus increase the specific measuring signal.

Figure 8:
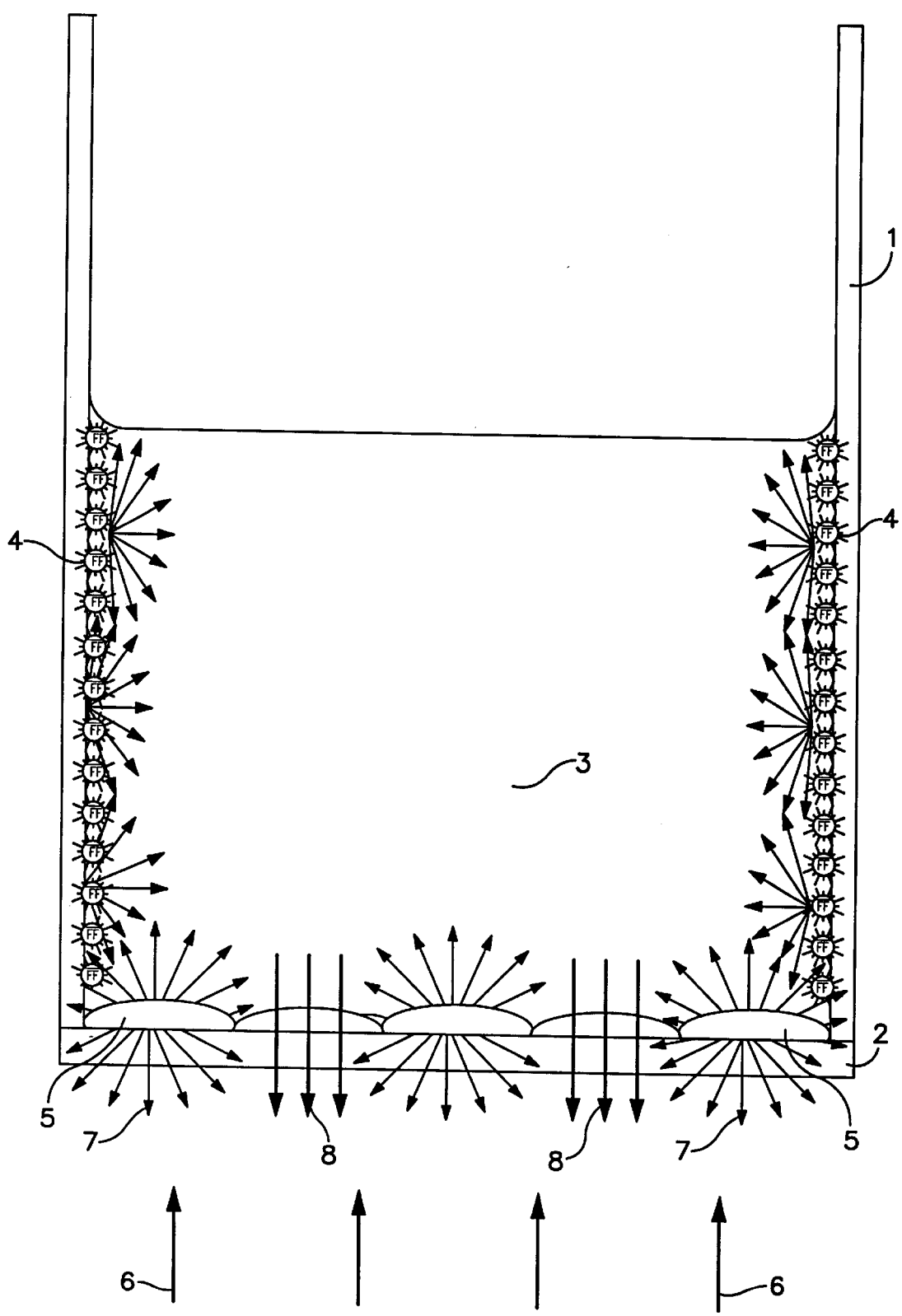
FIG. 8 shows the wall fluorescence in a fluorescence assay according to the prior art
Figure 9:
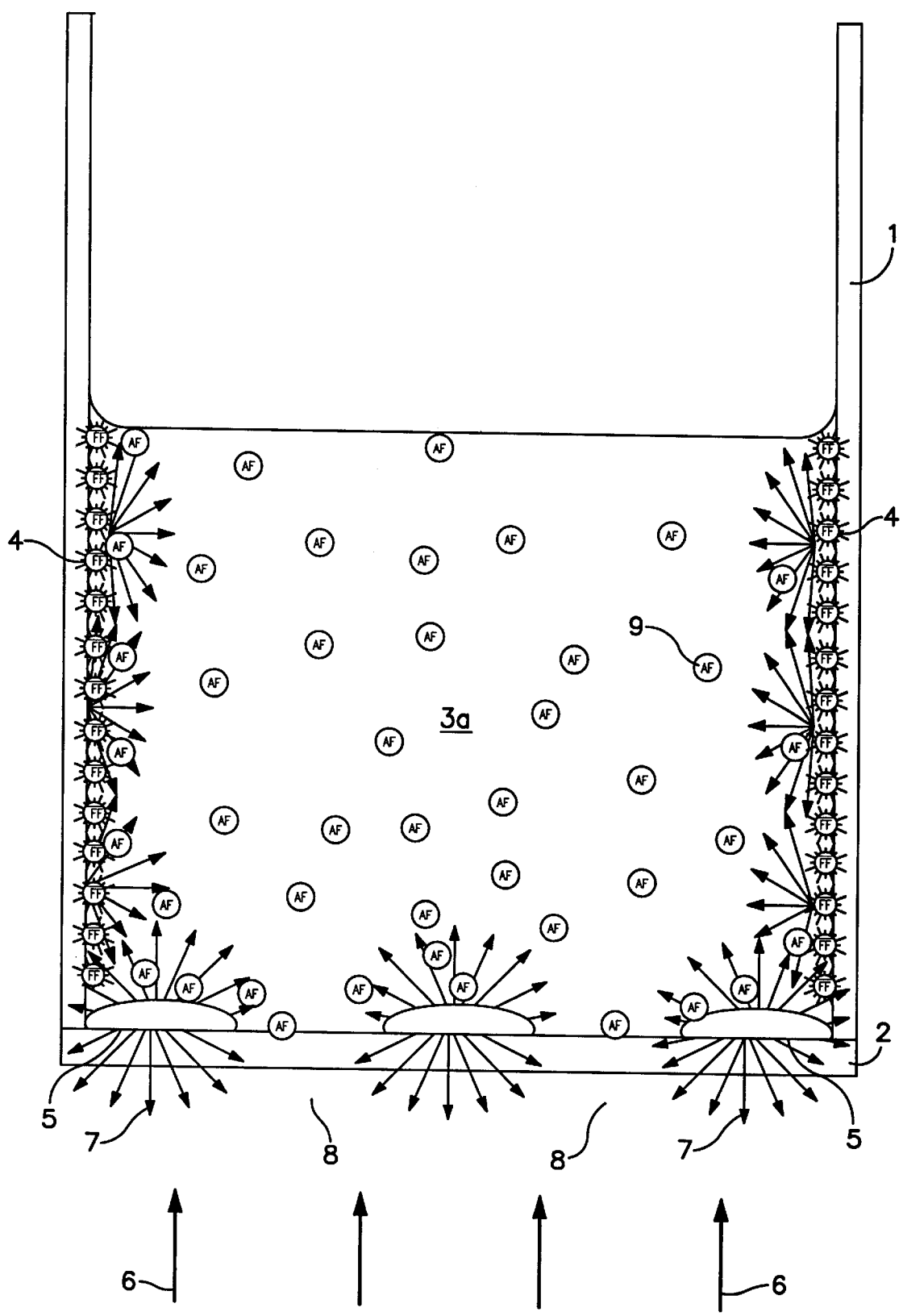
FIG. 9 shows the suppression of the wall fluorescence in a fluorescence assay with the aid of a masking dye and FIG. 10 shows the suppression of the background fluorescence or luminescence in a fluorescence or luminescence assay for the investigation of receptor-ligand binding with the aid of a masking dye in the supernatant

In a large number of other fluorescent test procedures on biological cells, it is possible, in contrast to dispersion dyes, to remove the fluorescent dye from the supernatant after staining of the cells by solution exchange. The fluorescent dye FURA2-AM is cleaved, for example, into the free dye after penetrating into the cell and in this case loses its cell membrane permeability. As a result, a concentration of the impermeable fluorescent dye in the cell occurs. In this case, the fluorescent supernatant 3 can be replaced by a fluorescent dye-free solution 3a without changing the specific cell fluorescence. The non-specific background fluorescence of the supernatant is removed in this manner. FURA2-AM, however, stains reaction vessels persistently (wall fluorescence) and thus produces another non-specific fluorescence signal which is comparable with the background fluorescence of dispersion dyes. This situation is shown in FIG. 8. In this case, the background fluorescence radiation 8 is attributed to the fluorescent dye molecules 4 adhering to the vessel walls. By incorporation of masking dyes in the fluorescent dye-free supernatant 3a, this non-specific fluorescence signal can also be completely suppressed.

Figure 10:
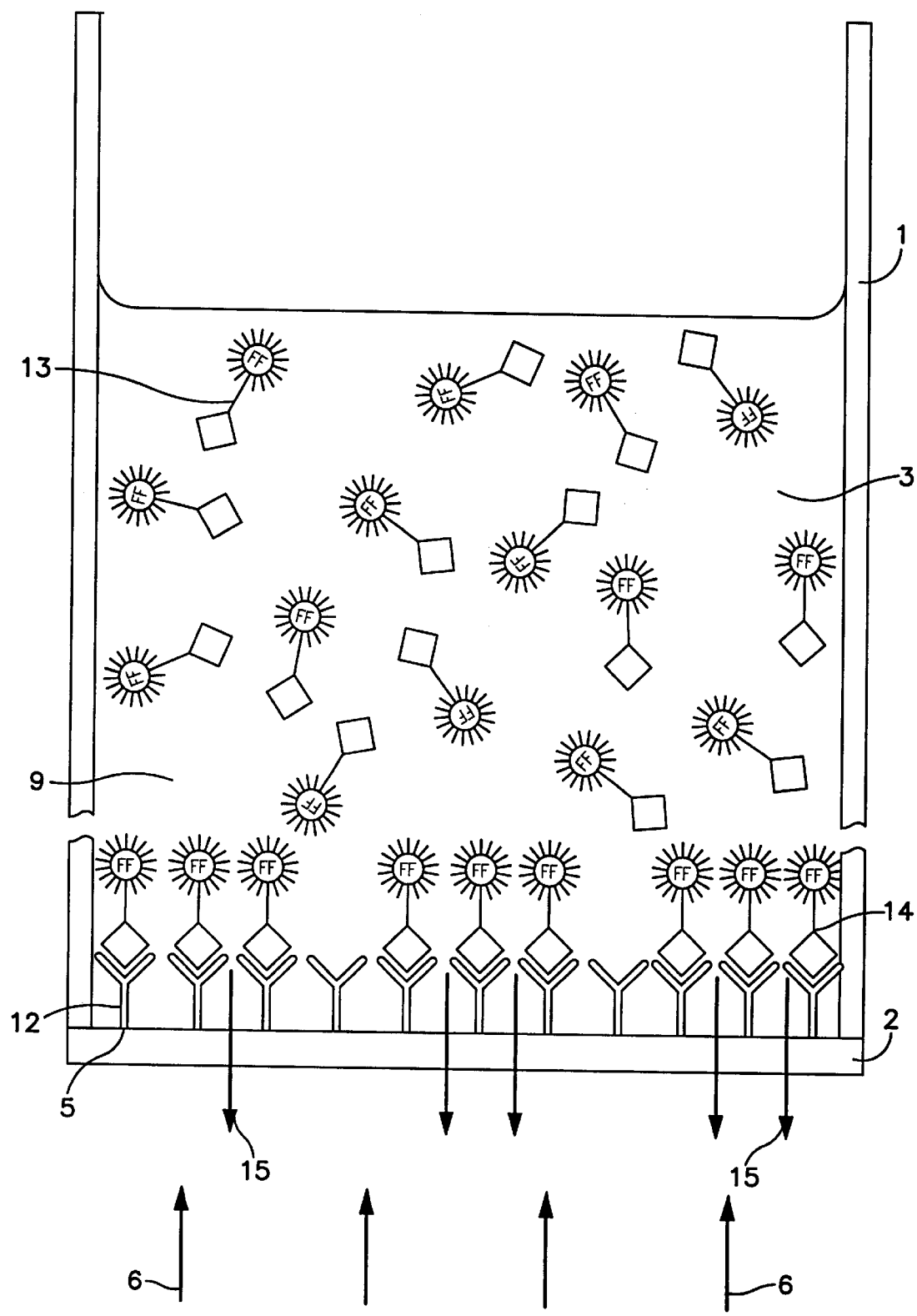
Figure 1:
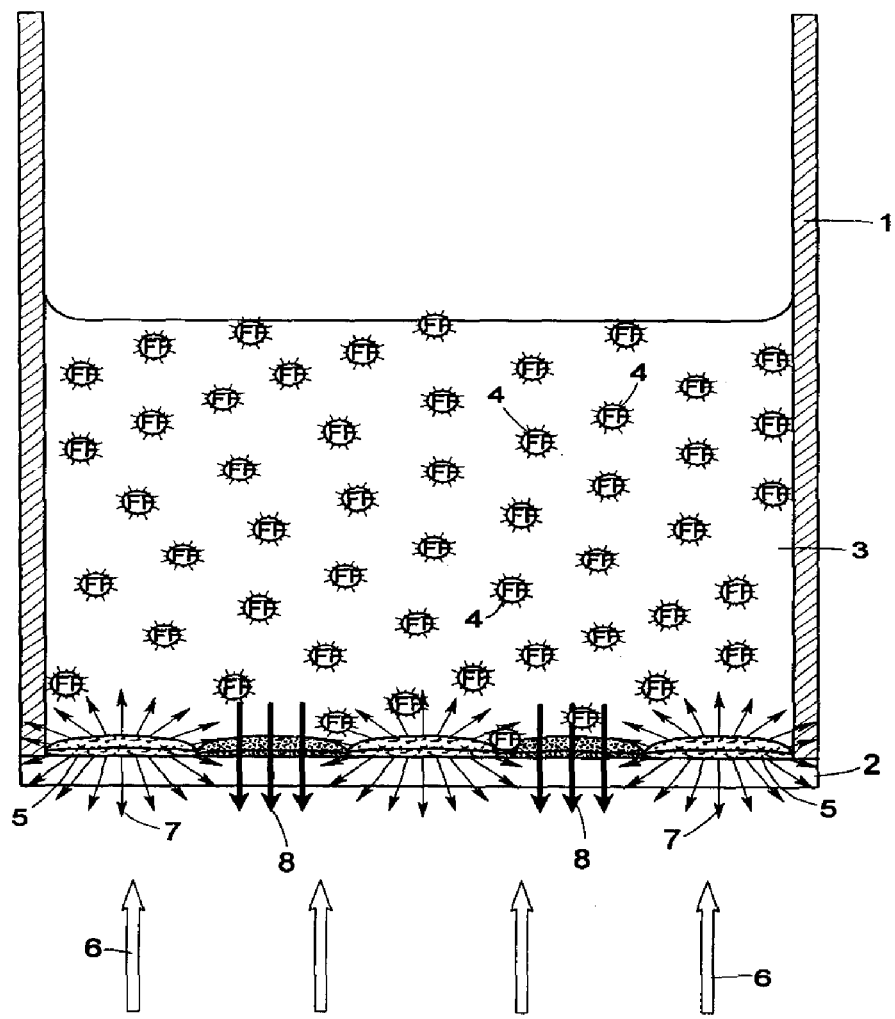
Figure 2:
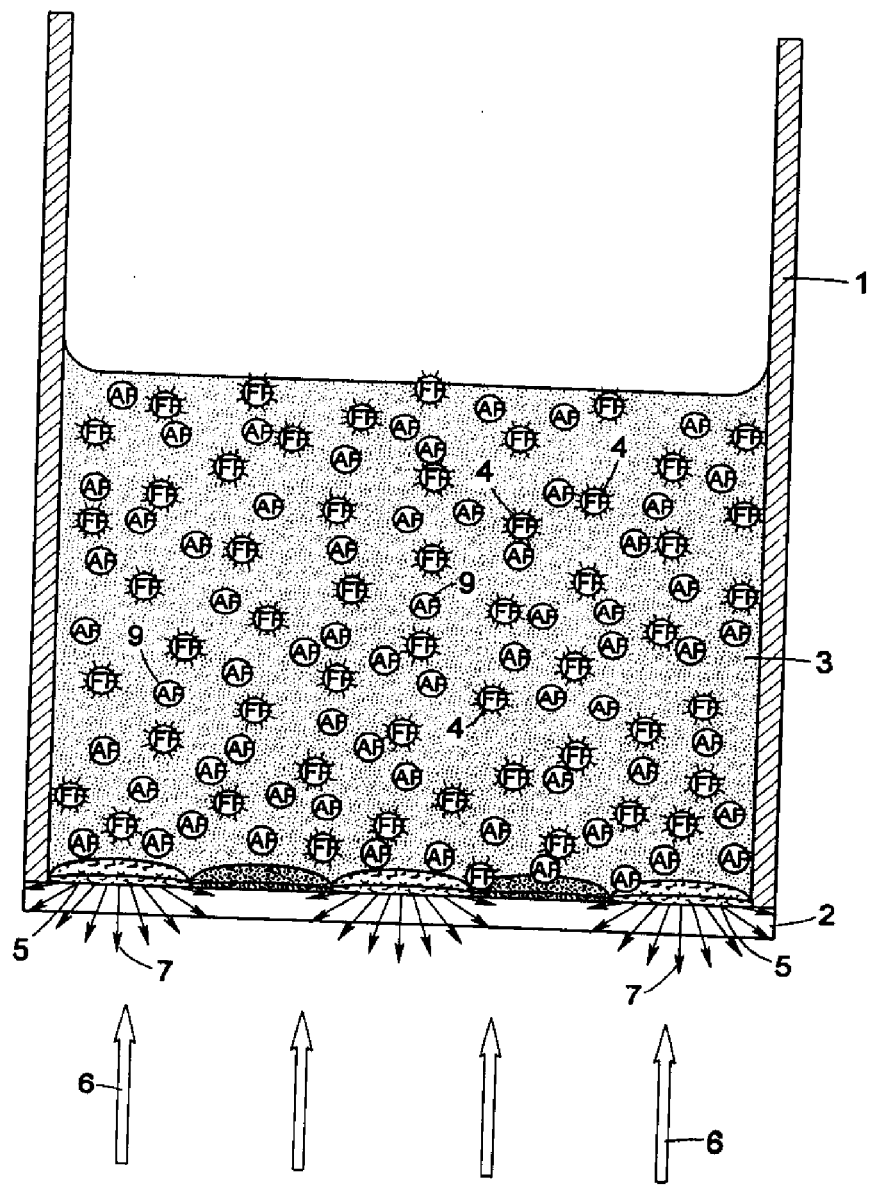
Figure 6:
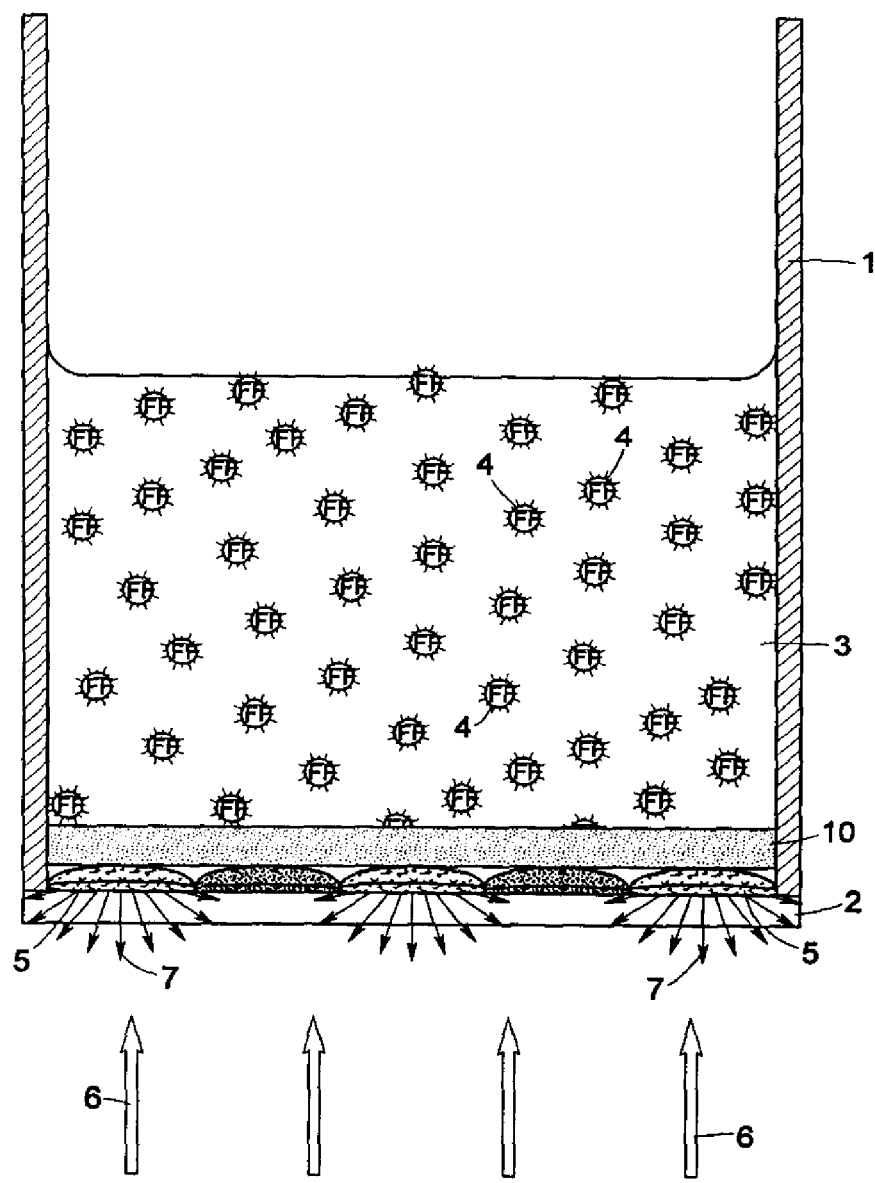
Figure 7:
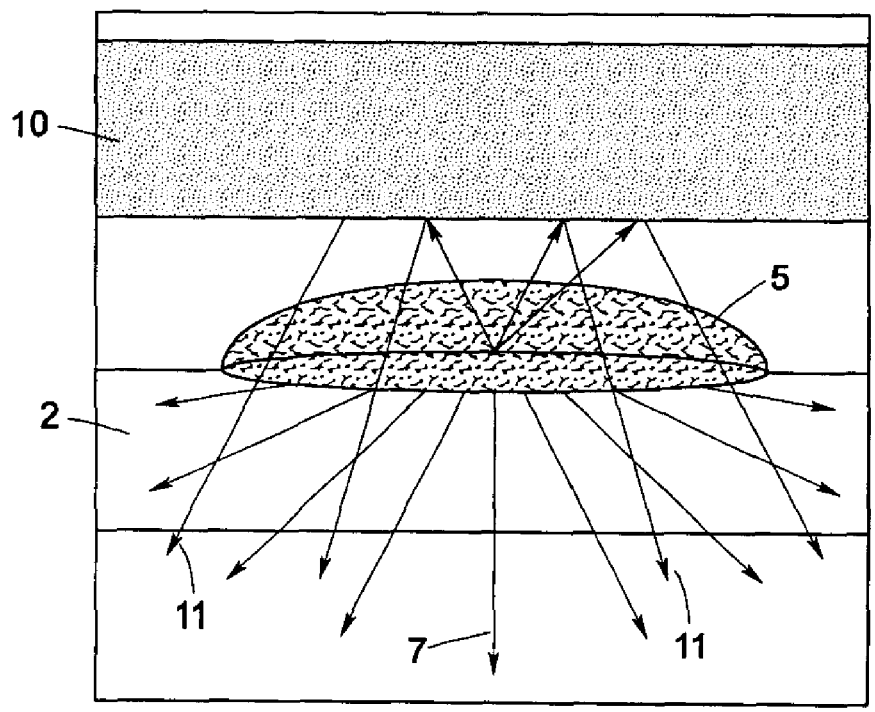
Figure 8:
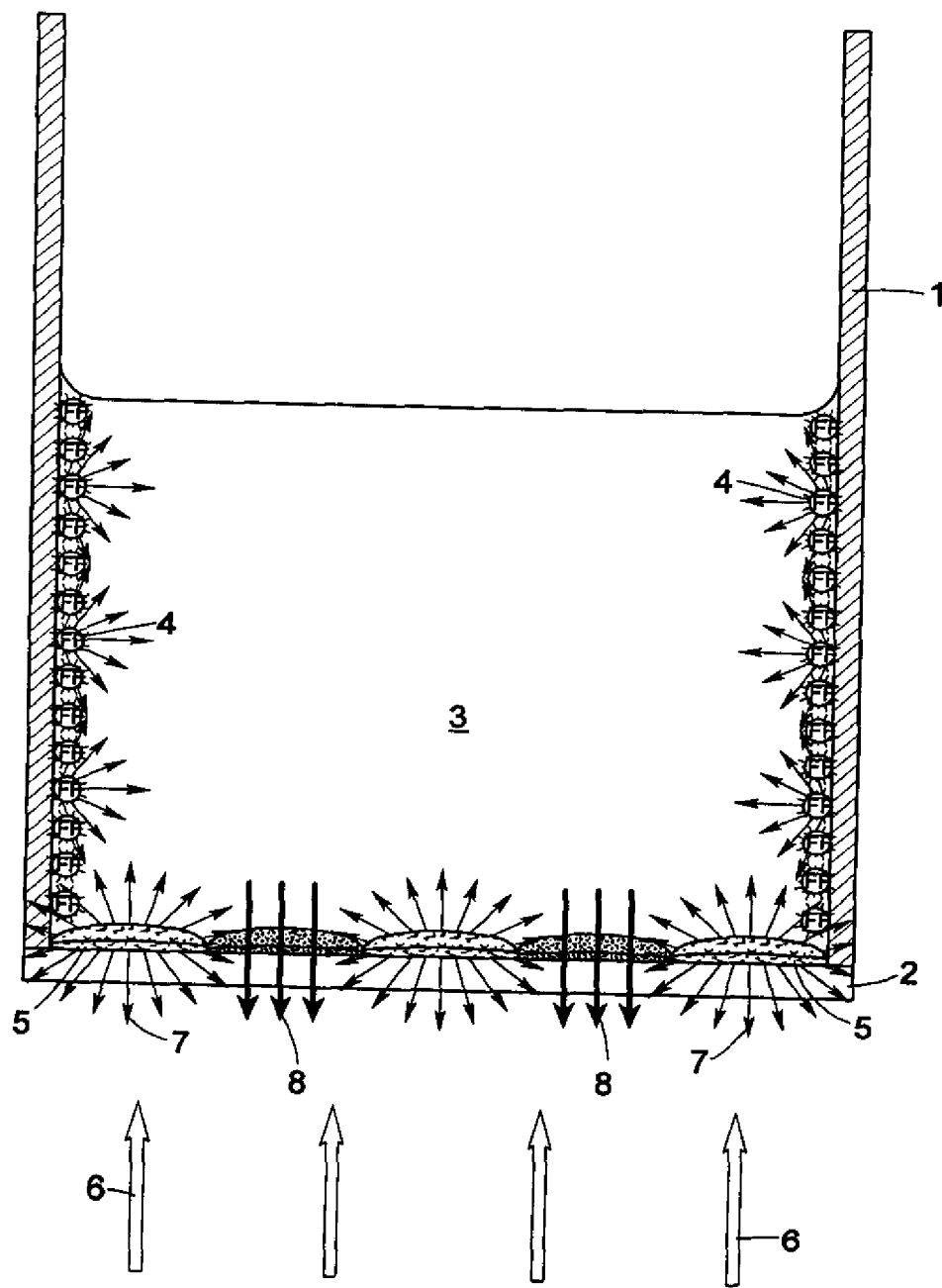
Figure 9:
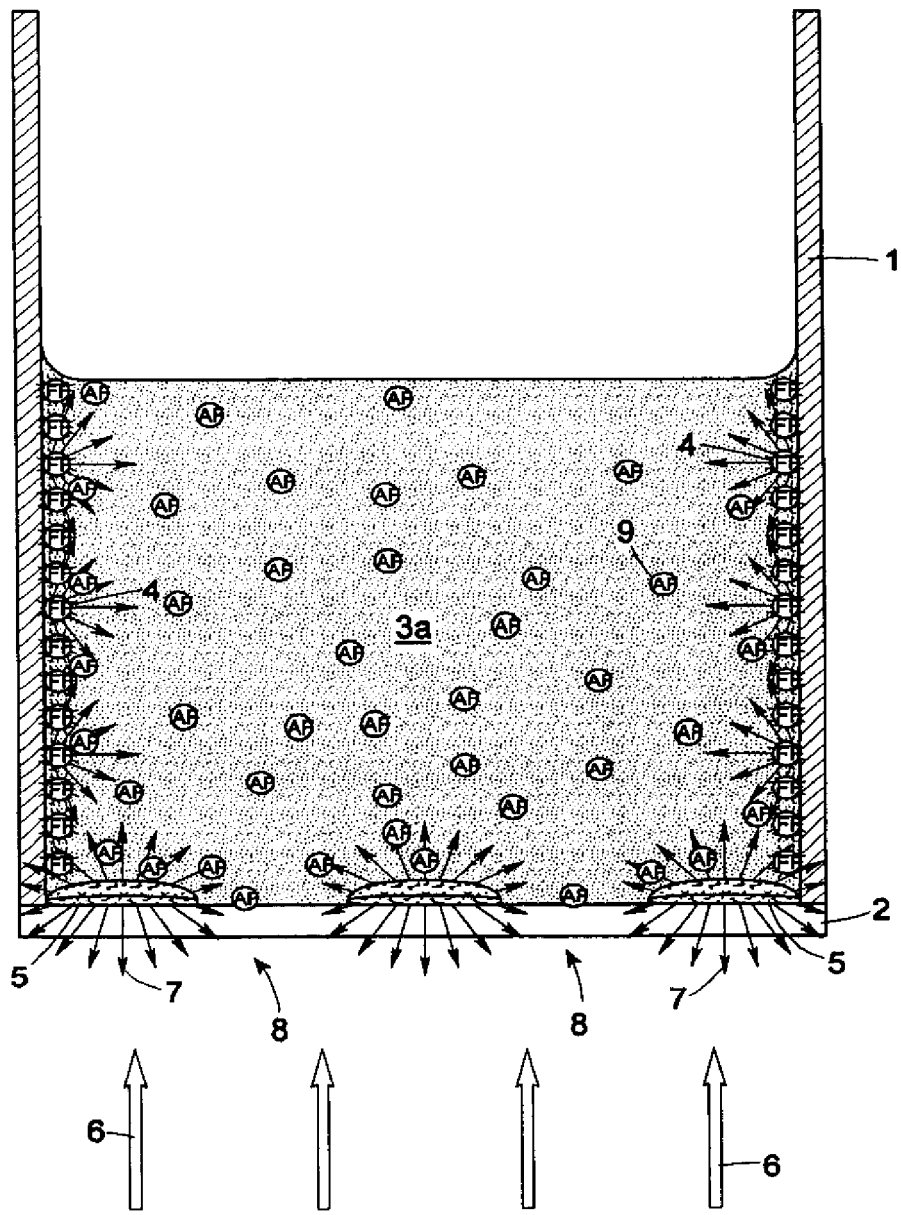

In FIG. 10, a working example analogous to FIG. 2 is additionally shown in which the biological layer applied to a transparent support at the bottom 2 of the reaction vessel 1 consists of receptors 12 which enter into a specific bond with the fluorescently or luminescently labelled ligand 13 present in the supernatant (solution) 3. The bound ligands are designated here by 14. In the case of the unlabelled solution, the primary light 6 shone through the bottom 2 excites the fluorescently labelled ligands 13 and 14 to fluorescence. In the case of luminescently labelled ligands, the primary light 6 is inapplicable. Analogously to the implementation according to FIG. 2, a masking dye which takes care that the fluorescent or luminescent radiation emitted from the unbound ligands 13 is completely absorbed in the solution is in turn added to the solution 3. The fluorescent or luminescent radiation 15 determined at the bottom 2, i.e. the measured effect, is therefore very predominantly attributed to the ligands 14 bound to the receptors 12 and is not adulterated by the background radiation of the unbound ligands 13 in the solution 3. The measuring signal is therefore a direct measure of the strength of the ligand-receptor binding. In this case, the layer thickness of the receptor layer is in the nm range, while the dimensions of the supernatant situated above it are in the order of magnitude of several mm.

Figure 7:
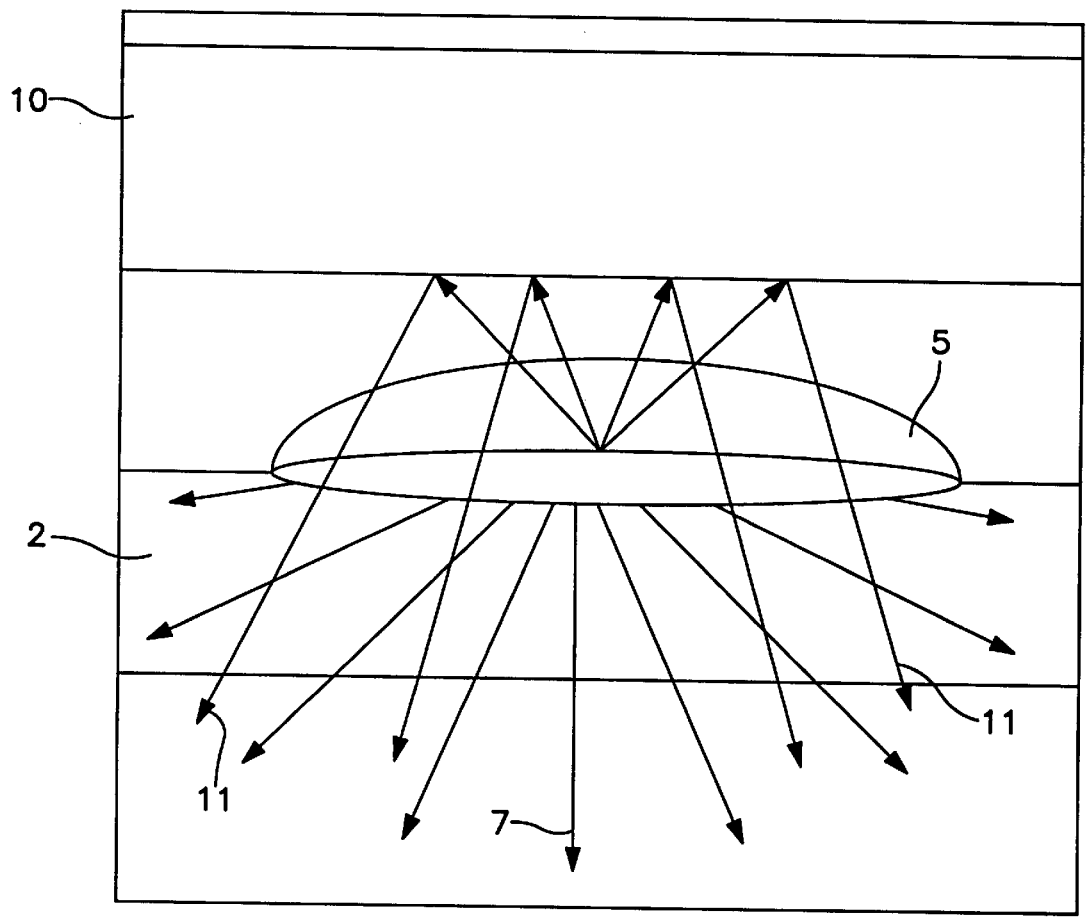
FIG. 7 shows the amplification of the luminescence by back-reflection from a separating layer

According to FIGS. 6 and 7, the separating layer 10 permeable to the solution can be employed in the investigation of ligand-receptor binding in an entirely analogous manner to the masking or suppression of the background fluorescence or luminescence. In this case, the interfering background fluorescence or luminescence is screened off by the separating layer 10 and in the case of luminescent ligands radiated fractions 11 of the luminescent light originating from bound ligands are reflected in the direction towards the reflector and thus the useful signal is increased.

The non-fluorescent or luminescent reaction component to be assessed with respect to its binding strength in classical pharmacological receptor binding studies was not shown here for reasons of clarity.

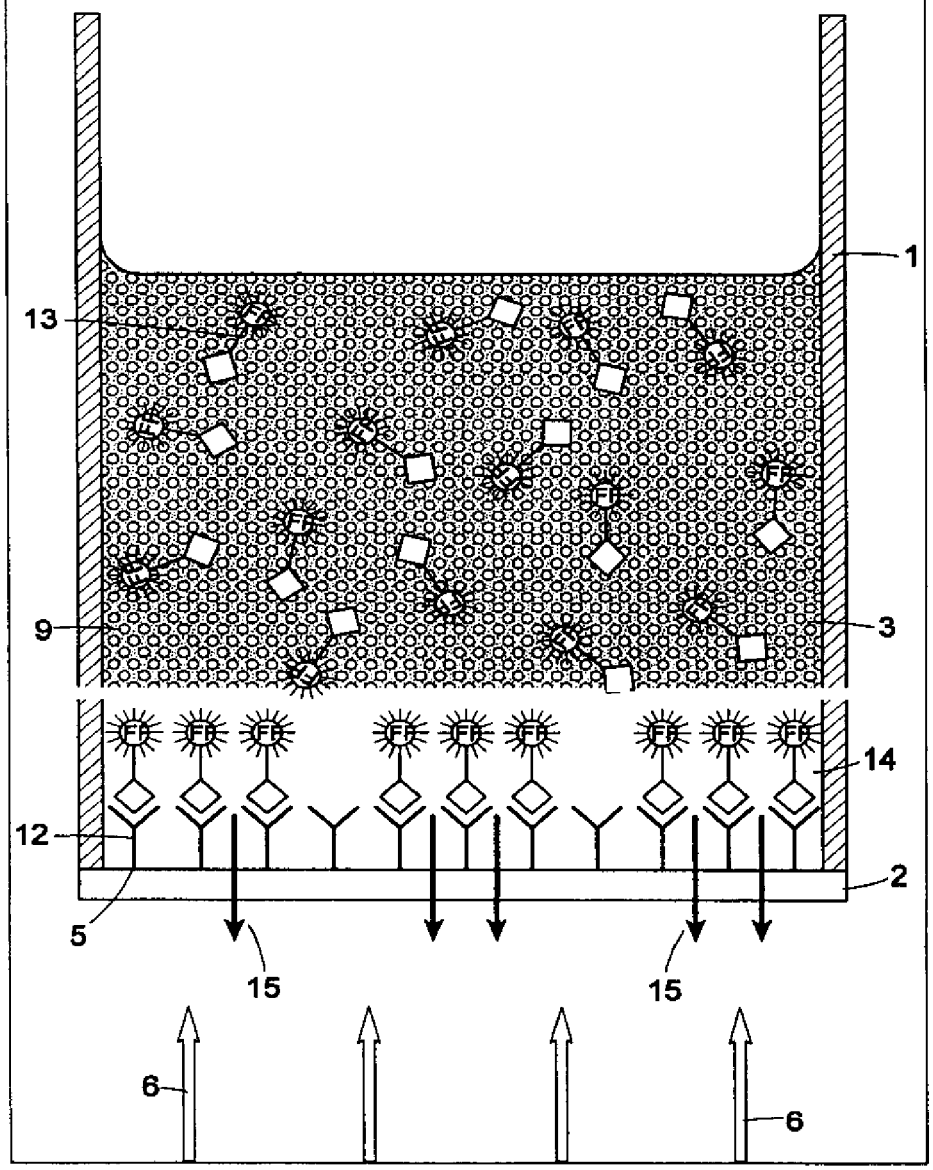

What is claimed is:

1. A process for the quantitative optical analysis of biological cells labeled with a fluorescent dye, the process comprising the following steps:
   a) applying a coherent layer of biological cells to a transparent support at the bottom of a reaction vessel;
   b) contacting the coherent layer of biological cells with a solution comprising a fluorescent dye to produce biological cells labeled with the fluorescent dye;
   c) shining excitation energy through the transparent support to cause the biological cells labeled with the fluorescent dye to exhibit fluorescene;
   d) adding to the solution comprising the fluorescent dye a masking dye, the masking dye absorbing at least one of:
      i) the excitation energy of the fluorescent dye in the solution; and
      ii) the emission light of the fluorescent dye in the solution; and
   e) detecting and analyzing the fluorescence of the biological cells labeled with the fluorescent dye through the transparent support;
   wherein steps c) and d) are carried out in any order.

2. The process according to claim 1, wherein the masking dye is water-soluble and has no cytotoxic side effects.

3. A process for the quantitative optical analysis of biological cells labeled with a fluorescent dye, the process comprising the following steps:
   a) applying a coherent layer of biological cells to a transparent support at the bottom of a reaction vessel;
   b) contacting the coherent layer of biological cells with a solution comprising a fluorescent dye to produce biological cells labeled with the fluorescent dye;
   c) shining excitation energy through the transparent support to cause the biological cells labeled with the fluorescent dye to exhibit fluorescene;
   d) applying to the coherent layer of biological cells a separating layer, the separating layer being permeable to the solution comprising the fluorescent dye, and the separating layer absorbing, reflecting or both absorbing and reflecting at least one of:
      i) the excitation energy of the fluorescent dye in the solution; and
      ii) the emission light of the fluorescent dye in the solution; and
   e) detecting and analyzing the fluorescence of the biological cells labeled with the fluorescent dye through the transparent support;
   wherein steps c) and d) are carried out in any order.

4. The process according to claim 3, wherein the separating layer comprises a layer of polymeric latex beads.

5. The process according to claim 4, wherein the polymeric latex beads are dyed with a masking dye.

6. The process according to claim 5, wherein the masking dye dyed on the polymeric latex beads is water-soluble and has no cytotoxic side effects.

7. A process for the quantitative optical analysis of biological cells labeled with a fluorescent dye, the process comprising the following steps:
   a) applying a coherent layer of biological cells to a transparent support at the bottom of a reaction vessel;
   b) contacting the coherent layer of biological cells with a solution comprisiing a fluorescent dye to produce biological cells labeled with the fluorescent dye;
   c) shining excitation energy through the transparent support to cause the biological cells labeled with the fluorescent dye to exhibit fluorescene;
   d) adding to the solution comprising the fluorescent dye a masking dye, the masking dye absorbing at least one of:
      i) the excitation energy of the fluorescent dye in the solution; and
      ii) the emission light of the fluorescent dye in the solution;
   e) applying to the coherent layer of biological cells a separating layer, the separating layer being permeable to the solution comprising the fluorescent dye, and the separating layer absorbing, reflecting or both absorbing and reflecting at least one of:
      i) the excitation energy of the fluorescent dye in the solution; and
      ii) the emission light of the fluorescent dye in the solutions; and
   f) detecting and analyzing the fluorescent of the biological cells labeled with the fluorescent dye through the transparent support;
   wherein steps c) through e) are carried out in any order.

8. The process according to claim 7, wherein the masking dye is water-soluble and has no cytotoxic side effects.

9. The process according to claim 7, wherein the separating layer comprises a layer of polymeric latex beads.

10. The process according to claim 9, wherein the polymeric latex beads are dyed with a masking dye.

11. The process according to claim 10, wherein the masking dye dyed on the polymeric latex beads is water-soluble and has no cytotoxic side effects.

12. A process for the quantitative optical analysis of biological cells labeled with a fluorescent dye, the process comprising the following steps:
   a) applying a coherent layer of biological cells to a transparent support at the bottom of a reaction vessel;
   b) contacting the coherent layer of biological cells with a solution comprising a fluorescent dye to produce biological cells labeled with the fluorescent dye;
   c) shining excitation energy through the transparent support to cause the biological cells labeled with the fluorescent dye to exhibit fluorescent;
   d) replacing the solution comprising the fluorescent dye by a fluorescent dye-free solution;
   e) adding a masking dye to the fluorescent dye-free solution, the masking dye masking non-specific fluorescence emitted from a wall of the reaction vessel; and f) detecting and analyzing the fluorescence of the biological cells labeled with the fluorescent dye through the transparent support;

wherein steps c) through e) are carried out in any order.

13. The process according to claim 12, wherein the masking dye is water-soluble and has no cytotoxic side effects.

14. A process for the quantitative optical analysis of luminescent biological cells, the process comprising the following steps:
   a) applying a coherent layer of luminescent biological cells to a transparent support at the bottom of a reaction vessel;
   b) providing a solution above the coherent layer of luminescent biological cells;
   c) applying to the coherent layer of luminescent biological cells a separating layer, the separating layer, the separating layer being permeable to the solution, and the separating layer reflecting luminescent radiation emitted by the coherent layer of luminescent biological cells; and
   d) detecting and analyzing the luminescent radiation emitted by the coherent layer of luminescent biological cells;

wherien steps b) and c) are carried out in any order.

15. The process according to claim 14, wherein the separating layer comprises a layer of polymeric latex beads.

16. The process according to claim 15, wherein the polymeric latex beads are dyed with a masking dye.

17. The process according to claim 16, wherein the masking dye dyed on the polymeric latex beads is water-soluble and has no cytotoxic side effects.

18. A process for the quantitative optical analysis of fluorescently or luminescently labeled reaction components, the process comprising the following steps:
   a) applying or depositing a layer of receptors specific for a fluorescent or luminescent ligand to a transparent support at the bottom of a reaction vessel;
   b) adding a solution comprising the fluorescent or luminescent ligand to the reaction vessel;
   c) shining excitation energy through the transparent support to cause the emission of fluorescent or luminescent radiation which is characteristic of the binding of the receptor and the ligand;
   d) adding to the solution comprising the fluorescent or luminescent ligand a masking dye, the masking dye masking the fluorescence or luminescence of any ligand remaining in the solution comprising the fluorescent or luminescent ligand; and
   e) detecting and analyzing the fluorescent or luminescent radiation emitted due to the binding of the receptor and the ligand;

wherein steps b) through d) are carried out in any order.

19. The process according to claim 18, wherein the masking dye is water-soluble and has no cytotoxic side effects.

20. A process for the quantitative optical analysis of fluorescently or luminescently labeled reaction componenets, the process comprising the following steps:
   a) applying or depositing a layer of receptors specific for a fluorescent or luminescent ligand to a transparent support at the bottom of a reaction vessel;
   b) adding a solution comprising the fluorescent or luminescent ligand to the reaction vessel;
   c) shining excitation energy through the transparent support to cause the emission of fluorescent or luminescent radiation which is characteristic of the binding of the receptor and the ligand;
   d) applying to the layer of receptors specific for a fluorescent or luminescent ligand a separating layer, the separating layer being permeable to the solution comprising the fluorescent or luminescent ligand, and the separating layer absorbing, reflecting or both absorbing and reflecting at least one of:
      i) the excitation energy of any ligand remaining in the solution comprising the fluorescent or luminescent ligand; and
      ii) the fluorescence or luminescence of any ligand remaining in the solution comprising the fluorescent or luminescent ligand; and
   e) detecting and analyzing the fluorescent or luminescent radiation emitted due to the binding of the receptor and the ligand;

wherein steps b) through d) are carried out in any order.

21. The process according to claim 20, wherein the separating layer comrpises a layer of polymeric latex beads.

22. The process according to claim 21, wherein the polymeric latex beads are dyed with a masking dye.

23. The process according to claim 22, wherein the masking dye dyed on the polymeric latex beads is water-soluble and has no cytotoxic side effects.

24. A process for the quantitative optical analysis of fluorescently or luminescently labeled reaction components, the process comprising the following steps:
   a) applying or depositing a layer of receptors specific for a fluorescent or luminescent ligand to a transparent support at the bottom of a reaction vessel;
   b) adding a solution comprising the fluorescent or luminescent ligand to the reaction vessel;
   c) shining excitation energy through the transparent support to cause the emission of fluorescent or luminescent radiation which is characteristic of the binding of the receptor and the ligand;
   d) adding to the solution comprising the fluorescent or luminescent ligand a masking dye, the masking dye masking the fluorescence or luminescence of any ligand remaining in the solution comprising the fluorescent or luminescent ligand;
   e) applying to the layer of receptors specific for a fluorescent or luminescent ligand a separating layer, the separating layer being permeable to the solution comprising the fluorescent or luminescent ligand, and the separating layer absorbing, reflecting or both absorbing and reflecting at least one of:
      i) the excitation energy of any ligand remaining in the solution comprising the fluorescent or luminescent ligand; and
      ii) the fluorescence or luminescence of any ligand remaining in the solution comprising the fluorescent or luminescent ligand; and
   f) detecting and analyzing the fluorescent or luminescent radiation emitted due to the binding of the receptor and the ligand;

wherein steps b) through e) are carried out in any order.

25. The process according to claim 24, wherein the masking dye is water-soluble and has no cytotoxic side effects.

26. The process according to claim 24, wherein the separating layer comprises a layer of polymeric latex beads.

27. The process according to claim 26, wherein the polymeric latex beads are dyed with a masking dye.

28. The process according to claim 27, wherein the masking dye dyed on the polymeric latex beads is water-soluble and has no cytotoxic side effects.

* * * * *

UNITED STATES PATENT AND TRADEMARK OFFICE
CERTIFICATE OF CORRECTION

PATENT NO. : 6,420,183 B1
DATED : July 16, 2002
INVENTOR(S) : Thomas Krahn et al.

It is certified that error appears in the above-identified patent and that said Letters Patent is hereby corrected as shown below:

Title page,
Item [75], Inventors, "Thoams Krahn" should read -- Thomas Krahn --.

Drawings,
Delete Drawing Sheets 1, 2, 6, and 7-10 and substitute therefor the attached Drawing Sheets 1, 2, 6, and 7-10.

Column 7,
Line 65, at the end of the line, the semi-colon (;) should be a colon (:).

Column 10,
Line 18, which is the second line of claim 21, "comprises" should be -- comprises --.

Signed and Sealed this

Nineteenth Day of April, 2005

JON W. DUDAS
*Director of the United States Patent and Trademark Office*